United States Patent [19]

Kienholz

[11] 4,367,182

[45] Jan. 4, 1983

[54] CONTAINER WITH INCORPORATED AERATOR

[75] Inventor: Charles M. Kienholz, San Dimas, Calif.

[73] Assignee: American Hospital Supply Corporation, Evanston, Ill.

[21] Appl. No.: 283,249

[22] Filed: Jul. 14, 1981

[51] Int. Cl.$^3$ .............................................. B01F 3/04
[52] U.S. Cl. ................................. 261/124; 261/122; 261/DIG. 65
[58] Field of Search ............... 261/DIG. 65, 124, 122, 261/77

[56] References Cited

U.S. PATENT DOCUMENTS

| | | | |
|---|---|---|---|
| 2,872,167 | 2/1959 | Pratt | 261/DIG. 65 |
| 2,998,671 | 9/1961 | Hinton | 261/121 M |
| 3,015,190 | 1/1962 | Arbeit | 261/77 |
| 3,446,353 | 5/1969 | Davis | 261/77 |
| 3,834,682 | 9/1974 | McPhee | 261/DIG. 65 |
| 3,903,216 | 9/1975 | Allan et al. | 261/DIG. 65 |
| 3,962,381 | 6/1976 | Farrish et al. | 261/DIG. 65 |
| 3,982,095 | 9/1976 | Robinson | 261/DIG. 65 |
| 4,036,919 | 7/1977 | Komendowski et al. | 261/DIG. 65 |
| 4,134,940 | 1/1979 | Sherman | 261/DIG. 65 |

FOREIGN PATENT DOCUMENTS 1569729  6/1980  United Kingdom ....... 261/DIG. 65

Primary Examiner—Tim R. Miles
Attorney, Agent, or Firm—Roger A. Williams

[57] ABSTRACT

A humidifier for humidifying gas with a liquid has a cavity defined by top, bottom, and side walls. An interior wall is attached to the side wall and defines a first and second cavity within the enclosed cavity. At least a first opening adjacent the bottom wall and at least a second opening adjacent the top wall extend through the interior wall to provide fluid flow communication between the first and second cavities. An enclosed conduit for the introduction of a gas to be humidified is secured to the side wall. The enclosed conduit has a closed end and an opening adjacent the closed end, which opening extends through the side wall of the humidifier adjacent the bottom wall and opens into the first cavity. The opening through the side wall provides for the formation of bubbles of a gas which are introduced into the humidifier through the enclosed conduit. An opening is provided through the top wall of the humidifier for exhausting the humidified gas from the humidifier. A tubular projection extends from the top wall and is in communication with the opening therethrough to provide for exhausting of the humidified gas.

13 Claims, 4 Drawing Figures

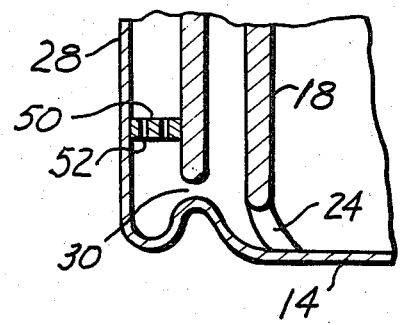

CONTAINER WITH INCORPORATED AERATOR

BACKGROUND OF THE INVENTION

The invention herein relates to a container having an aerator incorporated therein. In particular, the container herein has utility as a humidifier for supplying a liquid to a gas to be humidified.

Generally humidifiers find use in inhalation therapy. During inhalation therapy while a gas is being administered to a patient, such gas usually has a relatively low moisture content. The administration of a dry gas to a patient is undesirable as such a dry gas can dry out the nasal and other passageways through which the gas may travel.

Many humidifiers currently in use in inhalation therapy consist of a container containing a liquid to be added to the gas. Such containers are one-chamber containers having a gas sparger or gas diffuser either incorporated or inserted therein. Such diffusers or spargers are generally made from a porous material which is inserted or permanently affixed within the humidifier container. These diffusers provide small bubbles of gas which is bubbled through the liquid within the container. As the gas bubbles through the liquid, some of the liquid becomes associated or trapped within the gas, thus increasing the moisture content of the gas. After the gas bubbles have erupted through the surface of the liquid, the gas is expelled or withdrawn from the humidifier. The gas withdrawn from the humidifier has an increased amount of liquid vapor and can be delivered to the recipient for his therapy. It is desirable to use small bubbles of the gas being bubbled through the liquid as these small bubbles provide a relatively large surface exposure to the liquid, and thus increases the opportunity for absorption of the liquid by the gas.

As the gas is bubbled through the humidifier and the liquid absorbed by the gas, the volume of the liquid in the humidifier decreases due to such absorption. One drawback of humidifiers using such a technique for humidifying a gas is that the path of travel of the bubbles is through the liquid in the humidifier. As the volume of the liquid decreases, the path of travel of the gas bubbles also decreases, resulting in a reduction of air bubble exposure to the liquid. As the exposure of the gas bubbles to the liquid decreases, there is less uptake of the liquid by the bubbles. There is thus a lower output of the humidifier in terms of cubic centimeters per hour and milligrams of liquid vapor per liter of gas. Another drawback of such humidifiers is that such humidifiers are unable to provide for the total use of the liquid which they contain. That is, a bubble flow path through the liquid is necessary for absorption of the liquid by the gas, however, as the liquid volume decreases it reaches a critical level through which any gas bubbles will be unable to take up an efficacious amount of the liquid.

It would be desirable to provide a humidifier having a relatively constant path of travel for the gas bubbles through the liquid in order to provide for a relatively constant absorption of the liquid by the gas bubbles. Such a humidifier would also be desirable as it could provide for a relatively uniform concentration of liquid in the vapor being administered to a recipient during inhalation therapy.

SUMMARY OF THE INVENTION

The humidifier container herein has utility in inhalation therapy and can provide a relatively constant level of humidification of a gas being administered to a recipient. The humidifier herein comprises a container having a side wall, top wall and bottom wall. An interior wall within the container defines a first and second chamber within the container between the interior wall and side wall. The interior wall has at least a first opening adjacent the bottom wall and at least a second opening adjacent the top wall. The first and second openings extend through the interior wall providing fluid flow communication between the first and second chambers. Fastened to the container is an enclosed conduit closed at one end and having an opening adjacent the closed end and extending through the side wall and into the first chamber.

The opening extending through the side wall is of sufficient size to provide for bubbling of a gas introduced through the enclosed conduit and into the first chamber. That is, as a gas stream enters the enclosed conduit and flows from the conduit through the opening, the stream is interrupted and bubbles of the gas are formed.

A tubular projection is provided which extends outwardly from the top wall of the container. The tubular projection is in fluid flow communication with the second chamber of the container through an opening which extends through the top wall.

BRIEF DESCRIPTION OF THE DRAWINGS

FIG. 4 is a fractional side elevational view in cross section of another embodiment of the humidifier container.

DETAILED DESCRIPTION OF THE INVENTION

Figure 1:
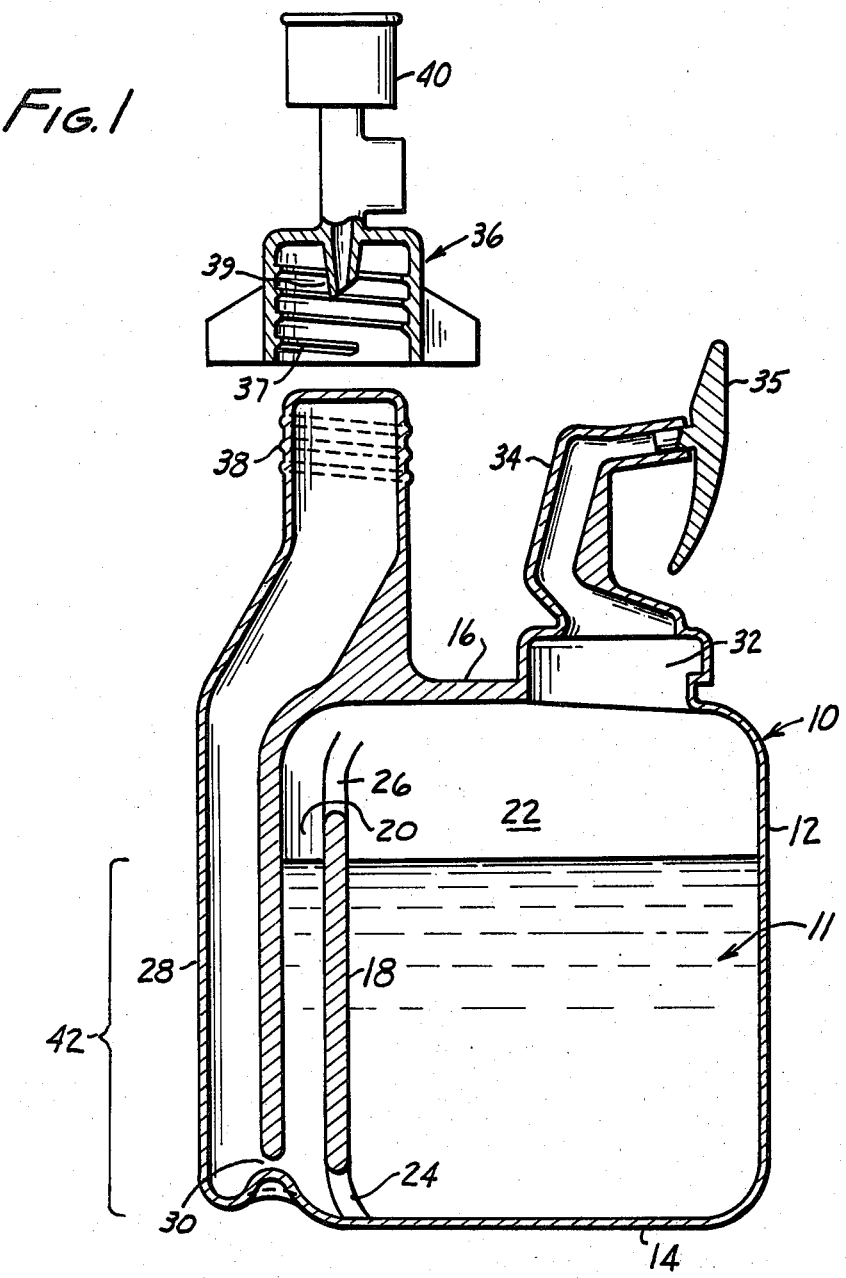
FIG. 1 is an exploded side elevational view in section of a humidifier container and cap.

In FIG. 1, a humidifier container 10 is shown in cross section. The humidifier container will hereinafter be referred to simply as container 10. The container 10 includes side wall 12, bottom wall 14 and top wall 16. The top, bottom and the side walls define an inner cavity within the container. Although the container is shown having a box-like configuration, it can have other configurations, such as cylindrical.

An interior wall 18 is provided within the container. The interior wall 18 can be secured to the side wall 12 and/or the top and bottom walls. The interior wall and side wall define a first chamber 20 and a second chamber 22 within the container. The interior wall is positioned within the container such that the first chamber 20 has a substantially lesser volume than the second chamber 22. The first chamber 20 has such a lesser volume as it is this first chamber that provides the flow path for gas bubbles through the liquid 11 present in the container as the humidifying liquid. The container is constructed for most humidification applications such that it provides a volume of from about 500 to about 1500 milliliters of such liquid.

The first chamber 20 of the container is in effect a lift chamber for the liquid 11 in the container. The liquid is lifted in first chamber 20 by the action of bubbles of gas flowing upwardly through the first chamber. This action is more fully explained hereinafter. The lifting effect provided by the first chamber is brought about by the configuration and size of the first chamber. That is, the volume and width is such that the bubbles formed tend to maintain a substantially constant volume (and thereby height) of liquid in the first chamber. In a working embodiment containing 500 ml of liquid, the first chamber had an oval lateral cross section having widths of 0.400 and 0.250 inches. For such a first chamber, the lifting effect created a liquid height of about 2.700 inches in the first chamber, which height remains substantially constant during use and relatively free from influence of the decrease in volume of liquid in the second chamber.

The interior wall has at least a first opening 24 and at least one second opening 26 which extend through the interior wall providing fluid flow communication between the first and second chambers. Such a first opening 24 is provided through the interior wall adjacent the bottom wall 14 of the container. Such a second opening 26 is provided through the interior wall adjacent the top wall 16 of the container. Such a first opening 24 permits liquid present in the container 10 to flow from the second chamber into the first chamber. The second opening 26 permits flow of a humidified gas from the space above the liquid in the first chamber into the space above the liquid level in the second chamber.

Figure 2:
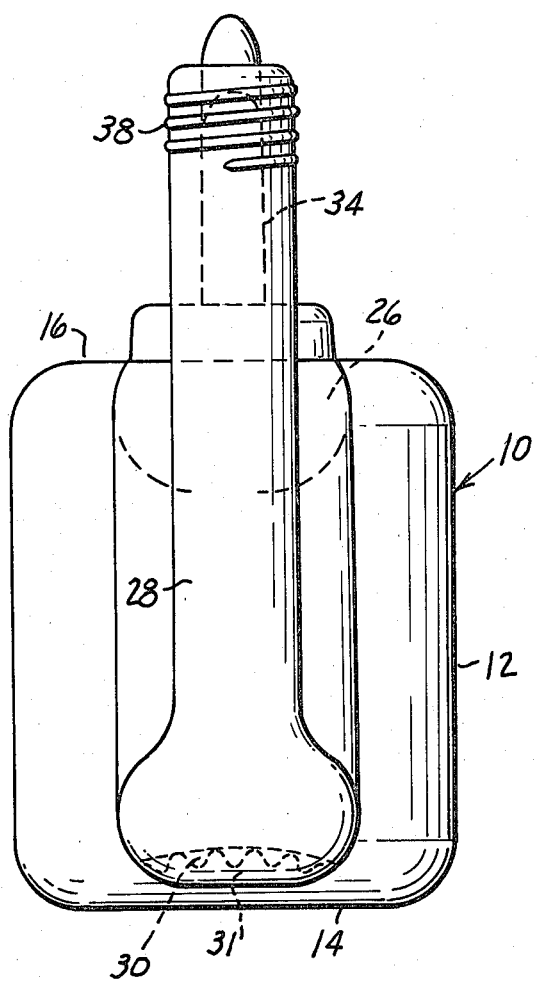
FIG. 2 is a side elevational view of the humidifier container of FIG. 1.
Figure 3:
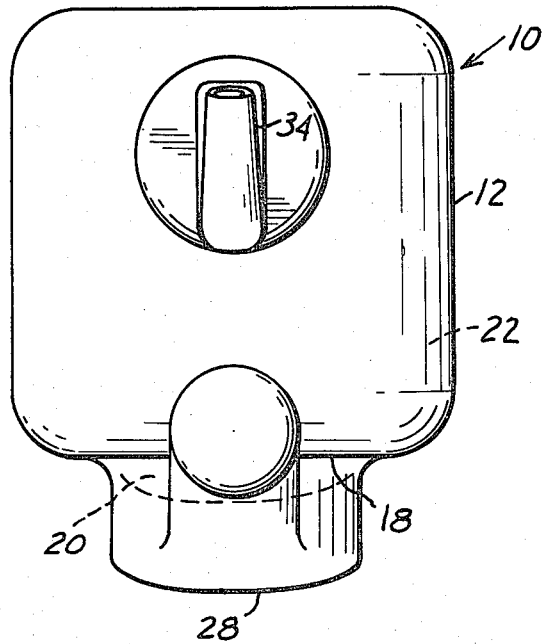
FIG. 3 is a top elevational view of the humidifier container of FIG. 1.

An enclosed conduit 28 closed at at least one end is secured to the container. Preferably, the enclosed conduit extends along a side wall of the container. The enclosed conduit 28 has an opening 30 adjacent the closed end which extends through the side wall 12 and into the first chamber of the container. The opening 30 is of such a size as to provide dispersion of a gas stream flowing along the enclosed conduit such that the gas flowing through the opening 30 is dispersed into bubbles. The dispersion of a gas into bubbles can be accomplished by creating a constriction at the opening 30. For example, a serrated opening as is more clearly shown in FIG. 2 can be provided. With regard to FIG. 2, the opening 30 is a serrated opening having serrations 31 along an edge of the opening. Such serrations restrict the flow of gas through the opening causing the gas to form bubbles in the liquid 11 within the container.

The bubbling of the gas can also be accomplished by placing a constriction in the enclosed conduit. As shown in FIG. 4, a perforated disk 50 having perforations 52 can be placed in the enclosed conduit. As a gas flows along the enclosed conduit, it encounters the perforated disk. As the gas passes through the perforated disk, it is interrupted to form bubbles as it enters the liquid medium.

A gas can also be caused to bubble by placing a constriction within the enclosed conduit. For example, a constriction such as a serrated constriction can be placed in the enclosed conduit adjacent the bottom wall 14 and opening 30. Such a serrated constriction could have a serrated opening such as the opening depicted as opening 30 in FIG. 2. However, the opening would be within the enclosed conduit 28. Preferably if such an opening is placed within the enclosed conduit 28, it would be spaced adjacent the bottom wall 14 adjacent opening 30 through the side wall. It is preferred to have the constricted opening adjacent the opening extending through the side wall such that the bubbles once formed would remain relatively small in order to provide as large a surface area as possible before absorption of the liquid. If the constriction is spaced away from the opening 30 through the side wall, there is greater possibility of the gas bubbles rejoining and forming bubbles of a larger size so as to reduce the surface area and ability of the gas bubbles to absorb liquid.

The opening 30 through the side wall is positioned along the side wall at a location spaced further away from the bottom wall 14 than the first opening 24 extending through the interior wall 18. That is, the opening through the side wall is positioned at a height within the liquid 11 greater than the height of the first opening 24 extending through the interior wall. The relative location of the opening 30 and first opening 24 are such that gas bubbles entering the liquid 11 through opening 30 tend to flow into and upwardly through first chamber 20 and the liquid 11 within the first chamber. If the first opening 24 were at about the same elevation or at a greater height than opening 30, some gas bubbles could flow through the first opening into the second chamber of the container. This would be undesirable as the flow path of such bubbles could not be maintained substantially constant.

An outlet for the humidified gas is provided on the container. For example, an opening or outlet 32 is provided extending through the top wall 16 of the container. Connected to the outlet is a tubular projection 34. The tubular projection is hollow, permitting flow of the humidified gas outwardly of the container. The tubular projection is adapted for connection to suitable elastomeric tubing. It is preferred that the tubular projection 34 be angled as is shown in FIG. 1. Such angles in the flow path of the humidified gas provide a tortuous pathway for the humidified gas which results in the removal of larger droplets of the liquid which may be carried by the gas. The outlet can be through either the side wall or top wall. It is preferable to place the outlet 32 such that it extends through the top wall 16 in order to provide an exhaust gas which is humidified but which has a relatively low proportion of entrained liquid droplets. By locating the outlet 32 along the top wall 16, another angle is placed within the flow path of the gas passing through the humidifier container.

The tubular projection 34 can be fitted with a plug or blocking element 35. The plug 35 can serve to maintain the contents within the container prior to use. For example, the plug 35 can be removed prior to use. When the humidifier container is made by molding, the plug can be integrally molded to the container such that it can be broken off prior to use.

It is preferred that the enclosed conduit 28 have an enclosed or covered end for adapting to a gas source. Such a closed end on the enclosed conduit prevents or inhibits the contamination of the liquid 11 within the container prior to use. The plug 35 also provides such protection.

The humidifier container herein can be provided with an adapter 36 for connection to a suitable gas source. The adapter 36 can be a threaded cap having threads 37 which engage appropriate threads 38 on the enclosed conduit. Within the cavity of the cap formed by the adapter 36 can be a projection 39. The projection 39 can be shaped such that upon threading the adapter 36 onto the enclosed conduit the projection pierces the enclosed conduit, providing fluid flow communication between a connector 40 secured to the adapter and the humidifier container 10. The connector 40 can be fitted with appropriate means for connection to a gas source or means for gas supply. For example, the connector 40 can be threaded for receiving suitable tubing from a gas supply.

In operation, the humidifier container is provided in a sterile condition to the user. The humidifier container contains a liquid 11 which will be used to humidify a gas being administered to the recipient. An adapter, such as the adapter 36, is threaded onto the humidifier container such that the projection within the adapter pierces the enclosed conduit of the humdifier container providing fluid flow communication between the gas source and the container. Plug 35 is removed from the tubular projection and a suitable tubing leading to the recipient is connected to the tubular projection 34.

The gas supply is activated and the gas flows through the connector 40 and into and through the enclosed conduit 28. As the gas flows through the enclosed conduit, it forces any liquid 11 in the conduit out of the conduit and into the humidifier container. The gas then flows through the opening 30 extending through the side wall of the humidifier container. As the gas flows through the opening 30, it forms bubbles of a relatively small size so as to provide a sufficient surface area for absorption of the liquid 11.

The opening 30 through the side wall is at a greater elevation with regard to the liquid level in the humidifier container than the first opening 24 extending through the interior wall. In view of the relative positions of these openings, the bubbles formed by the gas flowing through the opening 30 tend to flow upwardly through the first chamber 20 of the humidifier container. The bubbles have a sufficient size and velocity so as to maintain substantially the same liquid height, designated as 42, in such first chamber 20 during the use of the humidifier. In addition, the relative volumes of the first chamber 20 and the second chamber 22 are such that the first chamber is of a lesser volume such that the liquid height within the first chamber remains substantially the same as the gas bubbles therethrough. As the liquid 11 is absorbed by the gas, the volume of the liquid in the humidifier container decreases. Regardless of the decrease in volume of the liquid in the humidifier container, the liquid height in the first chamber 20 remains substantially the same. Of course, as the volume of liquid decreases to a level below the first opening 24 in the interior wall, there will be loss of height in the liquid level in the first chamber.

The gas bubbles flowing through the first chamber absorb some of the liquid within the chamber and thereby increase their moisture content. The bubbles erupt as humidified gas from the surface of the liquid and flow upwardly in the first chamber and through the second opening 26 in the interior wall. The humidified gas then flows through the outlet opening 32 and into and through the tubular projection 34. As the humidified gas flows through the second chamber and tubular projection, any large droplets of liquid entrained in the humidified gas can be removed by impingement of the humidified gas on the surfaces of the humidifier container and tubular projection. The humidified gas flowing to the recipient is therefore substantially void of undesirably large liquid droplets.

Although one embodiment has been described herein, modifications can be made without diverting from the concept. For example, a site can be provided on the container for introduction of an additional substance to the container. The configuration of the enclosed tubular conduit can also be varied such as by angling the portion of the conduit extending above the container. If such portion is angled toward the outlet, it can be possible to angle the container when in use such that the liquid will seek a low point in the container which will be the edge adjacent the first opening in the interior wall; i.e., the point of introduction of gas.

The container herein described can be constructed from any suitable material. Plastics such as polypropylene and polyethylene can be used. When such plastics are used, the container can be blow-molded using conventional blow-molding techniques.

The humidifier container herein described provides a container which can be adapted for use by an inhalation therapist which avoids the need for introducing an air sparger or disperser. The humidifier container herein also provides the inhalation therapist with a humidifier which can provide a humidified gas having a substantially constant liquid concentration as the flow path of the gas while it is absorbing liquid is substantially the same regardless of the total volume of the liquid in the container. In addition, the humidifier container herein described provides a humidifier container which can utilize a substantially large portion of the liquid volume initially present in the container.

I claim:

1. A humidifier container comprising:
    a side wall, top wall, bottom wall, and interior wall defining a first and second chamber within the container between the interior wall and side wall wherein the first chamber comprises a volume which maintains a substantially constant volume of liquid therein when gas is bubbled through such first chamber, and having at least a first opening adjacent the bottom wall and at least a second opening adjacent the top wall, which openings extend through the interior wall connecting the first and second chambers;
    an enclosed conduit closed at one end fastened to the container and including an opening adjacent the closed end extending through the side wall and into the first chamber of the container; and
    a tubular projection extending outwardly from the top wall and in communication with the second chamber through an opening extending through the top wall into the second chamber.

2. A humidifier container as recited in claim 1 wherein such first opening extending through the interior wall is positioned closer to the bottom wall than the opening extending through the side wall.

3. The humidifier container as recited in claim 1 wherein the opening extending through the side wall has a serrated edge.

4. A humidifier container as recited in claim 1 further comprising a perforated disk within the enclosed conduit.

5. A humidifier container as recited in claim 1 further comprising a serrated constriction within the enclosed conduit.

6. A humidifier container as recited in claim 1 wherein the enclosed conduit is closed at both ends.

7. A humidifier container as recited in claim 1 wherein the first chamber is substantially lesser in volume than the second chamber.

8. A humidifier container as recited in claim 1 further comprising an adapter for connecting the humidifier container with a gas supply, which adapter comprises a cap and means on such cap for connection to a gas source.

9. A humidifier for humidifying a gas with a liquid, the humidifier comprising:

an enclosed cavity defined by top, bottom and side walls;

a liquid within the enclosed cavity;

an interior wall attached to the side wall and defining a first and second cavity within the enclosed cavity wherein the first cavity has a volume sufficient for maintaining the liquid at about a constant volume in such first cavity, and having at least a first opening adjacent the bottom wall and at least a second opening adjacent the top wall, which openings extend through the interior wall to provide fluid flow communication between the first and second cavities;

an enclosed conduit for the introduction to the humidifier of a gas to be humidified, secured to the side wall, having a closed end and including an opening extending through the side wall adjacent the bottom wall into the first cavity;

means within the enclosed conduit for initiating bubbling of the introduced gas;

means within the humidifier for directing the gas bubbles into the first cavity; and means connected to the second chamber for exhausting a humidified gas from the second chamber.

10. A humidifier as recited in claim 9 wherein the means for directing the gas bubbles into the first cavity comprises an opening extending through the side wall further from the bottom wall than the first opening extending through the interior wall adjacent the bottom wall.

11. A humidifier as recited in claim 9 wherein the means for initiating bubbling of the introduced gas comprises constrictions within the opening extending from the enclosed conduit into the first cavity through the side wall adjacent the bottom wall.

12. A humidifier as recited in claim 11 wherein the constrictions in the opening comprise a serrated edge on the opening.

13. A humidifier for humidifying a gas with a liquid, the humidifier comprising:

an enclosed cavity defined by top, bottom and side walls;

an interior wall attached to the side wall and defining a first and second cavity within the enclosed cavity wherein the first cavity has a volume sufficient for maintaining a liquid present in the humidifier at about a constant volume in such first cavity, the interior wall having at least a first opening adjacent the bottom wall and at least a second opening adjacent the top wall, which openings extend through the interior wall to provide fluid flow communication between the first and second cavities;

an enclosed conduit for the introduction to the humidifier of a gas to be humidified, secured to the side wall, having a closed end and including an opening having a serrated edge, which opening extends through the side wall into the first cavity and which opening is spaced further from the bottom wall than the first opening extending through the interior wall; and an outlet in fluid flow communication with the second chamber for providing release of a humidified gas from the second chamber.

* * * * *